United States Patent
Tanaka

(10) Patent No.: US 7,716,607 B2
(45) Date of Patent: May 11, 2010

(54) AUTOMATIC ANALYZER

(75) Inventor: Kazuhiro Tanaka, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1055 days.

(21) Appl. No.: 11/324,276

(22) Filed: Jan. 4, 2006

(65) Prior Publication Data

US 2006/0145950 A1 Jul. 6, 2006

(30) Foreign Application Priority Data

Jan. 5, 2005 (JP) ............... 2005-000323

(51) Int. Cl.
G06F 3/048 (2006.01)

(52) U.S. Cl. .................... 715/867; 345/618

(58) Field of Classification Search ............... 715/867; 345/618
See application file for complete search history.

(56) References Cited

U.S. PATENT DOCUMENTS

| | | | | |
|---|---|---|---|---|
| 5,819,284 | A * | 10/1998 | Farber et al. | 709/203 |
| 6,067,570 | A * | 5/2000 | Kreynin et al. | 709/227 |
| 6,185,603 | B1 * | 2/2001 | Henderson et al. | 709/206 |
| 6,353,449 | B1 * | 3/2002 | Gregg et al. | 715/762 |
| 6,507,351 | B1 * | 1/2003 | Bixler | 715/810 |
| 6,633,318 | B1 * | 10/2003 | Kim et al. | 715/867 |
| 6,903,743 | B2 * | 6/2005 | Ng | 345/473 |
| 7,113,809 | B2 * | 9/2006 | Noesgaard et al. | 455/566 |
| 7,158,169 | B1 * | 1/2007 | Farber et al. | 348/173 |
| 7,384,601 | B2 * | 6/2008 | Matsubara et al. | 422/67 |
| 2003/0169306 | A1 * | 9/2003 | Makipaa et al. | 345/864 |
| 2004/0075701 | A1 * | 4/2004 | Ng | 345/867 |
| 2004/0221297 | A1 * | 11/2004 | Greve et al. | 719/318 |
| 2004/0224351 | A1 * | 11/2004 | Shinohara | 435/6 |
| 2004/0243682 | A1 * | 12/2004 | Markki et al. | 709/207 |
| 2005/0060670 | A1 * | 3/2005 | Inui et al. | 715/867 |
| 2006/0129947 | A1 * | 6/2006 | Hamzy et al. | 715/790 |

FOREIGN PATENT DOCUMENTS

| | | |
|---|---|---|
| EP | 0851232 A1 | 7/1998 |
| EP | 1291659 A2 | 3/2003 |
| EP | 2003-211799 | 7/2003 |
| EP | 2003-290196 | 10/2003 |
| JP | 2003-290196 | 10/2003 |

* cited by examiner

*Primary Examiner*—Richard Hjerpe
*Assistant Examiner*—Gregory J Tryder
(74) *Attorney, Agent, or Firm*—Mattingly & Malur, P.C.

(57) ABSTRACT

In an automatic analyzer for performing qualitative and quantitative analyses of living samples, such as blood and urine, a capability of recognizing the analyzer state, e.g., the state under run of analysis or the stopped state, from a distance is provided without increasing the cost. To realize that capability, the screen saver function of a display is modified to have the function of recognizing the analyzer state and reflecting the recognized analyzer state on a design of a screen image displayed with the screen saver function.

4 Claims, 3 Drawing Sheets

AUTOMATIC ANALYZER

BACKGROUND OF THE INVENTION

1. Field of the Invention

The present invention relates to an automatic analyzer for performing qualitative and quantitative analyses of living samples, such as blood and urine. More particularly, the present invention relates to an automatic analyzer provided with a display for displaying an operating screen.

2. Description of the Related Art

An automatic analyzer for analyzing the quantities of particular components in living samples, such as blood and urine, or detecting the presence of a particular antigen or antibody has been more increasingly employed primarily in large-scaled hospitals and test centers for the reasons that the automatic analyzer can more quickly perform measurements than manual operations and has higher reproducibility of the analysis results. In some of recent situations, a plurality of automatic analyzers are installed and operated by one clinic test operator for the purposes of increasing analysis efficiency and saving time and labor required.

In such a situation, the test operator has to check a display of each analyzer or come close to each analyzer to directly look the operating states of analyzer mechanisms in order to confirm conditions in the progress of analyses in the individual automatic analyzers.

In recent automatic analyzers, however, each analyzer is covered with a cover for safety or other reasons, and it is difficult to recognize the operating states of analyzer mechanisms by looking at them from a distance.

Also, when checking the display, the test operator is required to closely look at an image on a display screen and cannot recognize the operating state of each analyzer at a glance. Further, because recent displays usually have the screen saver function to prevent burning of the display screen, the image on the display screen cannot be viewed once the screen saver is started.

Though not being included in the technical field of the above-described automatic analyzer, Patent Document 1 (JP,A 2003-290196) discloses a medical image capturing system with the function of, when information to be notified of a user, such as run of image capturing or addition of a reservation, arrives via no input units, switching over a screen to be able to display that information even during the execution of a screen saver.

SUMMARY OF THE INVENTION

However, if any abnormality occurs in the system, the technique disclosed in Patent Document 1 cannot inform the abnormality by using the display screen. Also, an indicator lamp may be added to display the occurrence of an abnormality in the automatic analyzer, but this solution increases the cost.

An object of the present invention is to provide an automatic analyzer provided with a capability enabling an operator to recognize from a distance whether the analyzer is in the state under run of analysis or the stopped state, and/or whether there occurs any abnormality.

To achieve the above object, the present invention is constituted as follows.

The automatic analyzer comprises a storage unit for storing correspondence between a plurality of states of said automatic analyzer, including at least two analyzer states representing run and stop of analysis, and display designs displayed on an operating screen of the automatic analyzer; and a control unit for controlling, depending on the state of the automatic analyzer, the display design displayed on the operating screen in accordance with the correspondence between the analyzer states and the display designs, which is stored in the storage unit.

The analyzer state may include the occurrence of an abnormality. Also, the analyzer state may be divided into more detailed states indicating the progress of analysis, e.g., the state immediately after loading of a sample, the state during analysis, and the state capable of soon outputting the result. The display design may be a background color, for example, when data is displayed on the screen. As an alternative, when a screen saver image is displayed, the display design may be a pattern or design of the image displayed by a screen saver. In any case, it is essential that a plurality of different screen images are displayed so as to enable an operator to recognize the different analyzer states from a distance.

The automatic analyzer may have the function of allowing the design of the screen image to be freely set at the user's discretion. In addition, the automatic analyzer may have the function of generating sounds (playing music) depending on the design of the screen image displayed.

According to the present invention, it is possible to confirm the state of the automatic analyzer from a distance.

DESCRIPTION OF THE PREFERRED EMBODIMENTS

Figure 5:
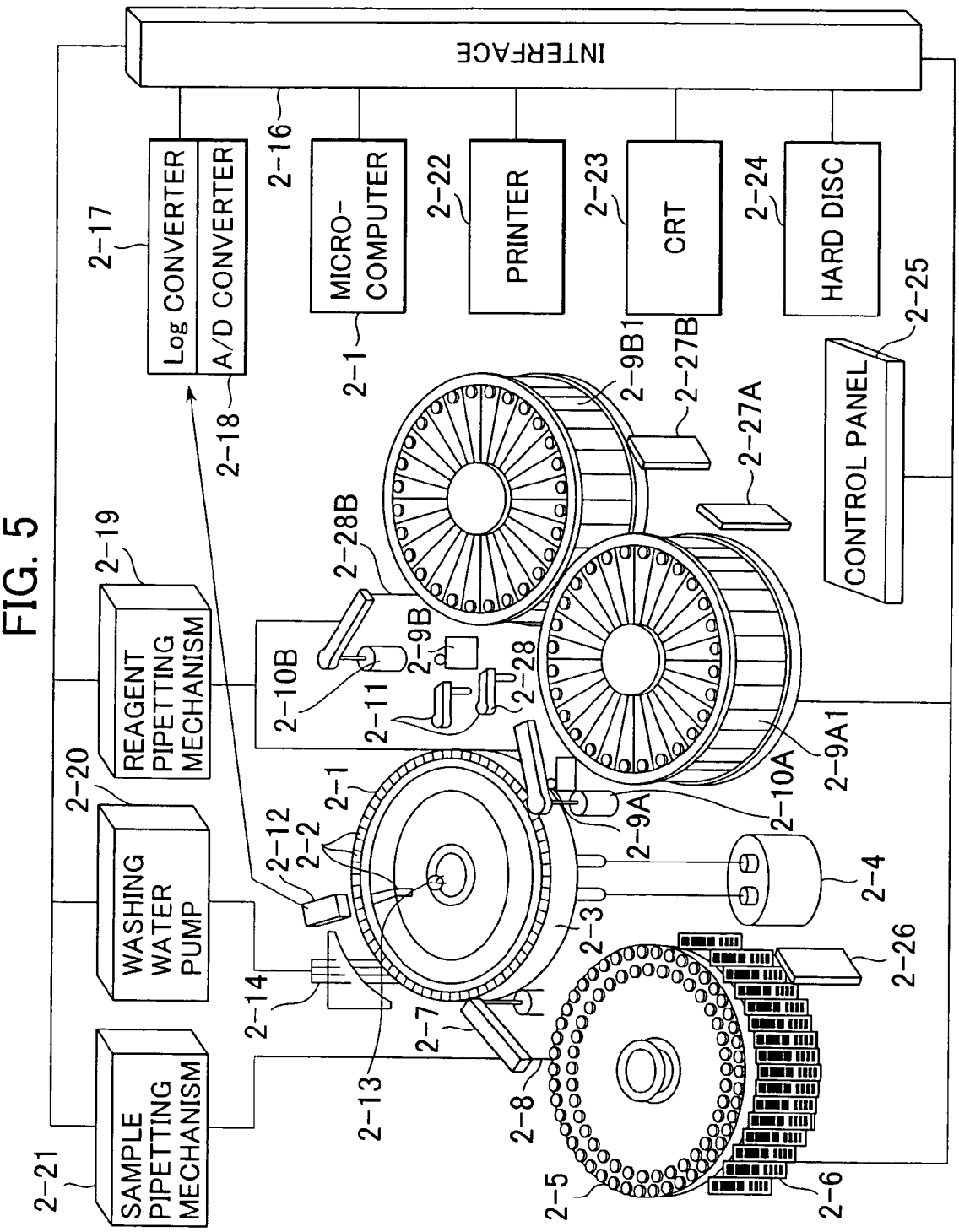
FIG. 5 is a schematic view showing the construction of the automatic analyzer.

FIG. 5 schematically shows a basic arrangement of an automatic analyzer. In FIG. 5, reference numeral 2-1 denotes a reaction disc. Reaction cuvettes 2-2 are placed on an outer peripheral portion of the reaction disc 2-1. The whole of the reaction disc 2-1 is held at a predetermined temperature by a reaction disc incubator 2-3.

Reference numeral 2-5 denotes a sample disc mechanism for holding samples. Many test tubes containing samples and having barcodes 2-6 affixed thereto are placed on the sample disc mechanism. The sample in each test tube affixed with the barcode 2-6 is extracted, as required, by a nozzle 2-8 of a sample pipetter 2-7, and is poured into the reaction cuvette 2-2 placed in a sample pipetting position. Reference numerals 2-9A1, 2-9B1 denote reagent disc mechanisms on which reagent bottles each affixed with a barcode label are placed. Barcode readers 2-27A, 2-27B are associated with the reagent disc mechanisms 2-9A1, 2-9B1, respectively. At the time of registering reagents, reagent bottle information is registered corresponding to positions of the reagent bottles by reading the respective barcodes. A second reagent pipetter 2-10A and a first reagent pipetter 2-10B are installed near the reagent disc mechanisms 2-9A1, 2-9B1, respectively. Stirrers 2-11 are also installed near the reagent disc mechanisms 2-9A1, 2-9B1. Reference numeral 2-12 denotes a multi-wavelength spectrometer, and 2-13 denotes a light source. The reaction cuvette 2-2 containing a photometric target is positioned between the multi-wavelength spectrometer 2-12 and the light source 2-13. Reference numeral 2-14 denotes a washing mechanism. A control system and a signal processing system include a microcomputer 2-15, an interface 2-16, a Log converter 2-17, and an A/D converter 2-18. Further, reference numeral 2-19 denotes a reagent pipetting mechanism, 2-20 denotes a washing water pump, and 2-21 denotes a sample pipetting mechanism. In addition, the control system includes a printer 2-22 for printing data, a CRT 2-23 for display, a hard disc 2-24 serving as a memory, and a control panel 2-25 (e.g., a keyboard or a pointing device such as a touch screen or a mouse) for entry of information.

In FIG. 5, the sample put in the test tube affixed with the barcode is pipetted in predetermined volume into the reaction cuvette 2-2 by using the nozzle 2-8 of the sample pipetter 2-7 in accordance with analysis parameters which have been previously inputted through the control panel and stored in a memory within the microcomputer 2-15.

Then, the reaction cuvette 2-2 containing the pipetted sample is moved to the reagent pipetting position by rotating the reaction disc 2-1. Thereafter, reagents are pipetted in predetermined volumes into the reaction cuvette 2-2 containing the pipetted sample by using respective nozzles of the reagent pipetters 2-10A, 2-10B in accordance with the analysis parameters which have been previously inputted through the control panel and stored in the memory within the microcomputer 2-15.

Then, the sample and the reagents are stirred and mixed with each other by using the stirrers 2-11.

When the relevant reaction cuvette 2-2 moves across the photometric position, the absorbance of the sample is measured by the multi-wavelength spectrometer 2-12. The measured absorbance is taken into the microcomputer 2-15 via the Log converter 2-17, the A/D converter 2-18, and the interface 2-16. The absorbance is converted to concentration data in accordance with a working curve obtained from the absorbance of a calibrator, which has been previously measured by a designated analytical method per test. The thus-measured concentration data for each component is outputted to the printer and/or the screen.

In the analyzing process based on the above-described principle, an operator sets various parameters necessary for the analyses, registers the samples, and confirms the analysis result on the screen (CRT) 2-23.

Figure 1:
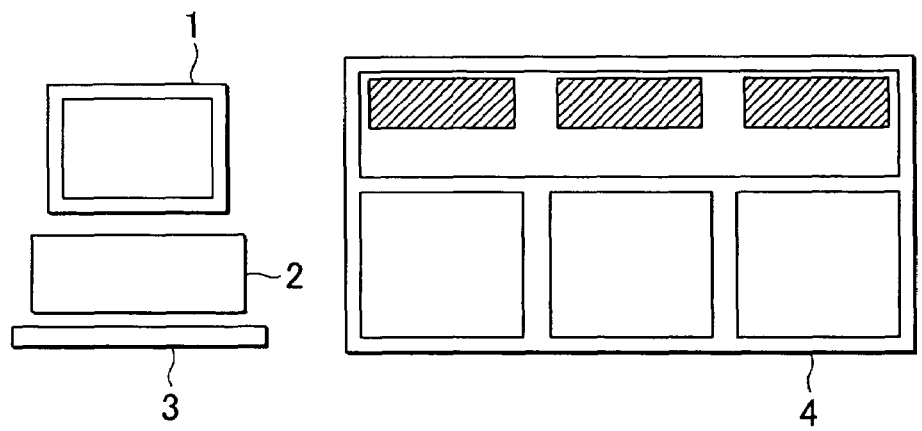
FIG. 1 shows an external appearance of an automatic analyzer.

In the automatic analyzer of the present invention, a section from which the operator operates the analyzer (referred to as an "operating section" hereinafter, which is denoted by 1, 2 and 3 in FIG. 1) and an analyzing section 4 are separated from each other. The operating section includes a display screen.

Figure 2:
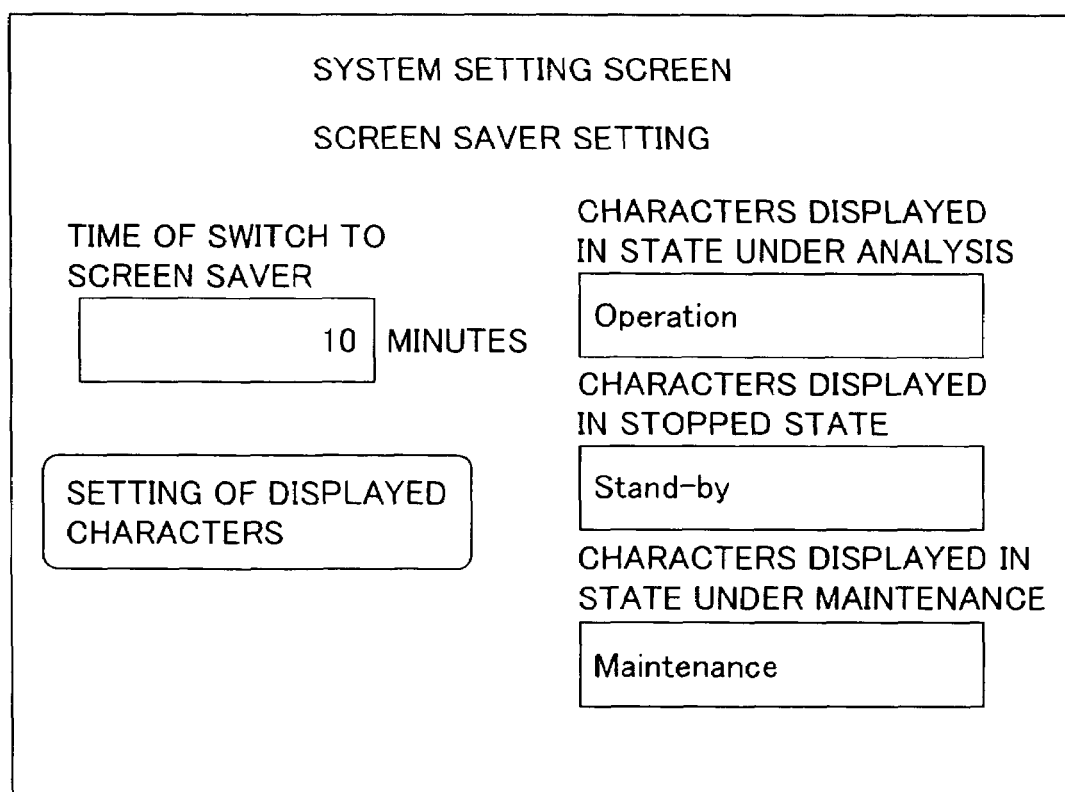
FIG. 2 shows an example of a screen-saver setting screen.

A screen saver used in the present invention can be set by selecting a screen-saver setting screen as one of various system setting screens displayed in accordance with software installed in the automatic analyzer (FIG. 2).

On the screen-saver setting screen, the operator is able to define a design (e.g., characters) displayed in the state under run of analysis, a design (e.g., characters) displayed in the stopped state, and the time of switch to the screen saver.

In the illustrated example, the design displayed in the state under run of analysis is set to "Operation", and the design displayed in the stopped state is set to "Stand-by". The time of switch to the screen saver is set to 10 minutes.

The font size, color, etc. of the displayed characters can be set at the operator's discretion on a child screen that is opened by selecting a button "setting of displayed characters".

Figure 3:
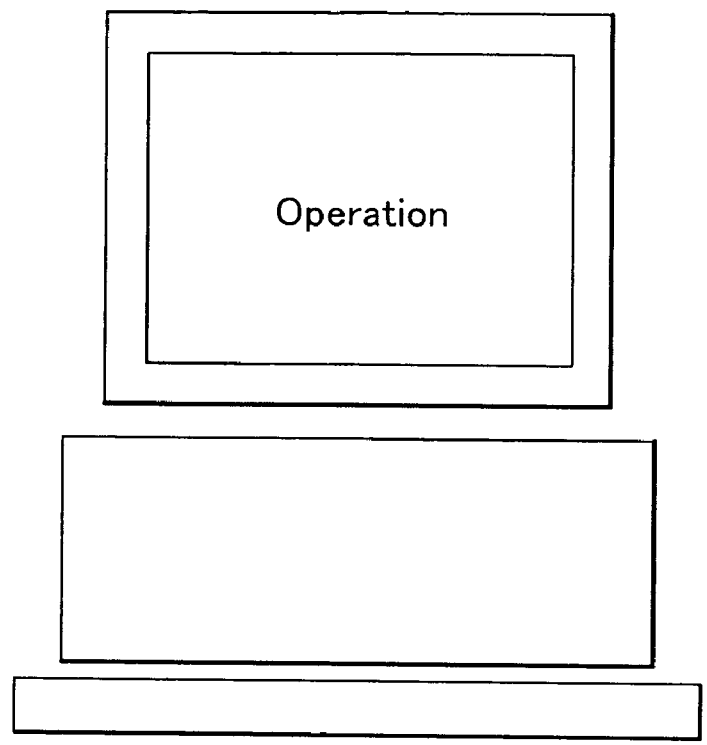
FIG. 3 shows an example of a screen saver image indicating the state under run of analysis.
Figure 4:
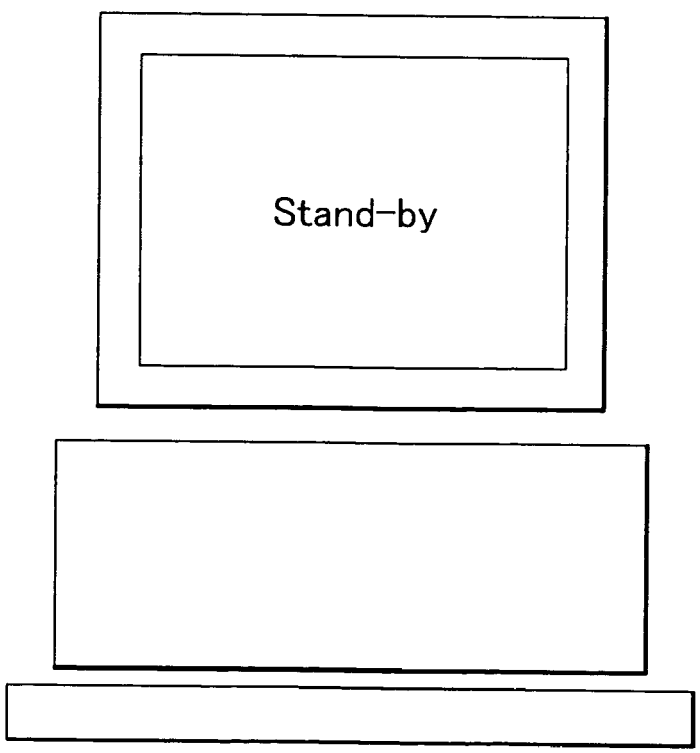
FIG. 4 shows an example of a screen saver image indicating the stopped (stand-by) state.

With the setting made in the illustrated example, when 10 minutes has lapsed after cease of input operations through the keyboard, the touch panel, etc., the state of the analyzer at that time is automatically determined. If the analyzer is in the state under run of analysis, a screen image as shown in FIG. 3 is displayed. Also, if the analyzer is in the stopped state, a screen image as shown in FIG. 4 is displayed. The characters, such as "Operation", in those screen images are designed not to reside in fixed positions on the display screen for the purpose of preventing burning of the display screen.

Also, during the execution of the screen saver, the screen saver continuously monitors the analyzer state. Accordingly, if the analyzer state is changed, for example, if the analyzer state is changed from the state under run of analysis to the stopped state, the screen image displayed by the screen saver and representing the analyzer state is also switched over from "Operation" to "Stand-by".

Then, if there comes any input from the input unit such as the keyboard or the touch panel, the screen saver is canceled and the screen image is returned to one displayed on the analyzer in an ordinary case.

Additionally, when the screen saver is employed as described above in the present invention, a screen saver originally contained in the operating system used by the computer in the operating section must be set to be not started.

Further, for an operator not employing the screen saver or in a period during which the screen saver is not executed, it is possible to make setting such that the background color of the ordinary operating screen is changed depending on the analyzer state. To that end, a setting screen for setting the background color depending on the analyzer state is also prepared.

With such a setting screen, the operator is able to select not only a mode for changing the background color depending on the analyzer state, but also a mode for blinking the background.

The above-described functions of monitoring the state, determining the monitored state, and displaying the determined state in accordance with screen saver software can be similarly applied to other technical fields without being limited to the automatic analyzer. For example, a screen saver capable of, when a computer executes image processing, determining whether the image processing has finished or not and displaying the determined result is convenient for users.

What is claimed is:

1. An automatic analyzer having a screen saver function displaying particular display design images on an operating screen when no input operation is made on said automatic analyzer for a predetermined time, comprising:

storage means for storing said particular display design images each of which corresponds to each of plural states of said automatic analyzer, respectively, said plural states including at least a first state of said automatic analyzer representing a running state of analysis and a second state of said automatic analyzer representing a stopped state of analysis; and control means for controlling the display of the particular display design images displayed on said operating screen in accordance with said plural states on the basis of a correspondence between said particular display design images and the plural states stored in said storage means, wherein said control means controls said operating screen to display one of said particular display design images corresponding to a first state of said automatic analyzer, and when a state of said automatic analyzer is changed during the execution of said screen saver function said control means controls said operating screen to display another of said particular display design images corresponding to a second state of said automatic analyzer different than the first state.

2. An automatic analyzer according to claim 1, wherein said particular display design images are background colors of a display screen image.

3. An automatic analyzer according to claim I, further comprising a changing means for changing the correspondence between the plural states of said automatic analyzer and the particular display design images on said operating screen.

4. An automatic analyzer according to claim 2, further comprising a changing means for changing the correspondence between the states of said automatic analyzer and the display design images on said operating screen.

* * * * *